US010813572B2

(12) United States Patent
Dohrmann et al.

(10) Patent No.: US 10,813,572 B2
(45) Date of Patent: Oct. 27, 2020

(54) INTELLIGENT SYSTEM FOR MULTI-FUNCTION ELECTRONIC CAREGIVING TO FACILITATE ADVANCED HEALTH DIAGNOSIS, HEALTH MONITORING, FALL AND INJURY PREDICTION, HEALTH MAINTENANCE AND SUPPORT, AND EMERGENCY RESPONSE

(71) Applicant: Electronic Caregiver, Inc., Las Cruces, NM (US)

(72) Inventors: Anthony Dohrmann, Las Cruces, NM (US); David W. Keeley, Frisco, TX (US); Robert Salcido, Las Cruces, NM (US); James Mitchell, Las Cruces, NM (US)

(73) Assignee: Electronic Caregiver, Inc., Las Cruces, NM (US)

( * ) Notice: Subject to any disclaimer, the term of this patent is extended or adjusted under 35 U.S.C. 154(b) by 355 days.

(21) Appl. No.: 15/530,185

(22) Filed: Dec. 9, 2016

(65) Prior Publication Data

US 2018/0160942 A1 Jun. 14, 2018
US 2018/0360349 A9 Dec. 20, 2018

Related U.S. Application Data

(60) Provisional application No. 62/386,768, filed on Dec. 11, 2015.

(51) Int. Cl.
*A61B 5/00* (2006.01)
*A61B 5/11* (2006.01)
(Continued)

(52) U.S. Cl.
CPC .......... *A61B 5/1117* (2013.01); *A61B 5/0013* (2013.01); *A61B 5/0077* (2013.01);
(Continued)

(58) Field of Classification Search
CPC .......... G06F 3/017; G06F 3/011; G06F 3/012; G06F 3/0346; G06F 3/0482; G06T 7/20;
(Continued)

(56) References Cited

U.S. PATENT DOCUMENTS 6,665,647 B1 12/2003 Haudenschild
7,233,872 B2 6/2007 Shibasaki et al.
(Continued)

FOREIGN PATENT DOCUMENTS

WO WO2018032089 A1 2/2018
WO WO2019143397 A1 7/2019
(Continued)

OTHER PUBLICATIONS

"International Search Report" and "Written Opinion of the International Searching Authority," Patent Cooperation Treaty Application No. PCT/US2018/057814, dated Jan. 11, 2019, 9 pages.
(Continued)

*Primary Examiner* — May A Abouelela
(74) *Attorney, Agent, or Firm* — Carr & Ferrell LLP

(57) ABSTRACT

A system for monitoring and detecting the gait and other health related parameters of a user. One such parameter is monitoring of medication compliance and treatment session attendance done by a medication and liquid dispensing apparatus, which combines mechanical dispensing of medication. These parameters are provided in standard of care summaries to care providers, and are continually reported by the Optimum Recognition Blueprint as Standard of Care Summaries to care providers, as well as communicated to the end-user by the Virtual Caregiver Interface.

4 Claims, 8 Drawing Sheets

(51) Int. Cl.
    *A61B 5/103*     (2006.01)
    *A61B 5/1171*     (2016.01)
    *A61B 5/0205*     (2006.01)

(52) U.S. Cl.
    CPC .......... *A61B 5/1036* (2013.01); *A61B 5/1127* (2013.01); *A61B 5/1128* (2013.01); *A61B 5/1176* (2013.01); *A61B 5/4833* (2013.01); *A61B 5/4866* (2013.01); *A61B 5/7275* (2013.01); *A61B 5/746* (2013.01); *A61B 5/749* (2013.01); *A61B 5/02055* (2013.01)

(58) Field of Classification Search
    CPC ............ G02B 27/017; G02B 2027/014; A61B 5/0077; A61B 2562/0219; A61B 5/0013; A61B 5/11; A61B 5/1117; A61B 5/746; A61B 5/0022; A61M 2021/005
    USPC ........................ 600/300, 587, 595; 340/573.1
    See application file for complete search history.

(56) References Cited

U.S. PATENT DOCUMENTS

| | | | |
|---|---|---|---|
| 7,612,681 B2 | 11/2009 | Azzaro et al. | |
| 8,206,325 B1 | 6/2012 | Najafi et al. | |
| 8,771,206 B2* | 7/2014 | Gettelman | A61B 5/744 600/587 |
| 9,591,996 B2 | 3/2017 | Chang et al. | |
| 10,628,635 B1 | 4/2020 | Carpenter, II et al. | |
| 2002/0062342 A1 | 5/2002 | Sidles | |
| 2002/0196944 A1 | 12/2002 | Davis et al. | |
| 2004/0109470 A1 | 6/2004 | Derechin et al. | |
| 2005/0035862 A1* | 2/2005 | Wildman | A61B 5/1113 340/573.1 |
| 2007/0238936 A1 | 10/2007 | Becker | |
| 2009/0094285 A1 | 4/2009 | Mackle et al. | |
| 2011/0126207 A1* | 5/2011 | Wipfel | H04L 9/3213 718/104 |
| 2012/0025989 A1* | 2/2012 | Cuddihy | G06K 9/00369 340/573.1 |
| 2012/0075464 A1* | 3/2012 | Derenne | A61B 5/0013 348/135 |
| 2012/0120184 A1 | 5/2012 | Fornell et al. | |
| 2012/0154582 A1 | 6/2012 | Johnson et al. | |
| 2012/0179067 A1* | 7/2012 | Wekell | A61B 5/0002 600/587 |
| 2012/0229634 A1* | 9/2012 | Laett | G08B 21/043 348/143 |
| 2013/0127620 A1* | 5/2013 | Siebers | A61M 5/142 340/573.1 |
| 2013/0167025 A1 | 6/2013 | Patri et al. | |
| 2013/0204545 A1 | 8/2013 | Solinsky | |
| 2013/0212501 A1 | 8/2013 | Anderson et al. | |
| 2013/0237395 A1* | 9/2013 | Hjelt | A63B 22/18 482/146 |
| 2013/0289449 A1* | 10/2013 | Stone | A61B 5/112 600/595 |
| 2014/0128691 A1 | 5/2014 | Olivier | |
| 2014/0148733 A1* | 5/2014 | Stone | A61B 5/004 600/595 |
| 2014/0171834 A1 | 6/2014 | DeGoede et al. | |
| 2014/0232600 A1* | 8/2014 | Larose | G01S 5/0205 342/463 |
| 2014/0243686 A1* | 8/2014 | Kimmel | A61B 5/1114 600/476 |
| 2014/0278605 A1 | 9/2014 | Borucki et al. | |
| 2014/0337048 A1 | 11/2014 | Brown et al. | |
| 2015/0109442 A1* | 4/2015 | Derenne | G06F 16/78 348/143 |
| 2015/0359467 A1 | 12/2015 | Tran | |
| 2016/0217264 A1 | 7/2016 | Sanford | |
| 2016/0253890 A1 | 9/2016 | Rabinowitz et al. | |
| 2016/0267327 A1 | 9/2016 | Franz et al. | |
| 2017/0000422 A1 | 1/2017 | Moturu et al. | |
| 2017/0140631 A1 | 5/2017 | Pietrocola et al. | |
| 2017/0147154 A1* | 5/2017 | Steiner | G06F 3/0481 |
| 2017/0192950 A1 | 7/2017 | Gaither et al. | |
| 2017/0213145 A1 | 7/2017 | Pathak et al. | |
| 2017/0337274 A1 | 11/2017 | Ly et al. | |
| 2017/0344706 A1 | 11/2017 | Torres et al. | |
| 2018/0189756 A1 | 7/2018 | Purves et al. | |
| 2018/0322405 A1 | 11/2018 | Fadell et al. | |
| 2019/0029900 A1 | 1/2019 | Walton et al. | |
| 2019/0116212 A1 | 4/2019 | Spinella-Mamo | |
| 2019/0220727 A1 | 7/2019 | Dohrmann et al. | |
| 2019/0259475 A1 | 8/2019 | Dohrmann et al. | |
| 2019/0282130 A1 | 9/2019 | Dohrmann et al. | |
| 2019/0311792 A1 | 10/2019 | Dohrmann et al. | |
| 2019/0385749 A1 | 12/2019 | Dohrmann et al. | |
| 2020/0251220 A1 | 8/2020 | Chasko | |

FOREIGN PATENT DOCUMENTS

| | | |
|---|---|---|
| WO | WO2019164585 A1 | 8/2019 |
| WO | WO2019182792 A1 | 9/2019 |
| WO | WO2019199549 A1 | 10/2019 |
| WO | WO2019245713 A1 | 12/2019 |
| WO | WO2020163180 A1 | 8/2020 |

OTHER PUBLICATIONS

"International Search Report" and "Written Opinion of the International Searching Authority," Patent Cooperation Treaty Application No. PCT/US2018/068210, dated Apr. 12, 2019, 9 pages.

Dohrmann, Anthony et al., "Computing Devices with Improved Interactive Animated Conversational Interface Systems," U.S. Appl. No. 16/169,760, dated Oct. 24, 2018, Specification, Claims, Abstract, and Drawings, 32 pages.

"International Search Report" and "Written Opinion of the International Searching Authority," Patent Cooperation Treaty Application No. PCT/US2019/021678, dated May 24, 2019, 12 pages.

"International Search Report" and "Written Opinion of the International Searching Authority," Patent Cooperation Treaty Application No. PCT/US2019/025652, dated Jul. 18, 2019, 11 pages.

"International Search Report" and "Written Opinion of the International Searching Authority," Patent Cooperation Treaty Application No. PCT/US2019/034206, dated Aug. 1, 2019, 11 pages.

Rosen et al., "Slipping and Tripping: Fall Injuries in Adults Associated with Rugs and Carpets," Journal of Injury & Violence Research, 5(1), (2013), pp. 61-69.

Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.

Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.

Bellemare et al., A Distributional Perspective on Reinforcement Learning:, Proceedings of the 34th International Conference on Machine Learning, Sydney, Australia, Jul. 21, 2017, 19 pages.

Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS ONE 4(7): e6421>, 13 pages.

Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.

"International Search Report" and "Written Opinion of the International Searching Authority," Patent Cooperation Treaty Application No. PCT/US2020/016248, dated May 11, 2020, 7 pages.

* cited by examiner

INTELLIGENT SYSTEM FOR MULTI-FUNCTION ELECTRONIC CAREGIVING TO FACILITATE ADVANCED HEALTH DIAGNOSIS, HEALTH MONITORING, FALL AND INJURY PREDICTION, HEALTH MAINTENANCE AND SUPPORT, AND EMERGENCY RESPONSE

PRIORITY

This application claims benefit of earlier filed provisional Ser. No. 621386,768, Date of Filing Dec. 11, 2015.

BACKGROUND OF THE INVENTION

1. Field of the Invention

This invention relates to a system of automated electronic caregiving assistance and health monitoring.

2. Description of the Prior Art

In recent years, personal emergency response systems ("PERS") have been developed which offer a single button, worn or the wrist, a belt or around the neck, which allows a user to summon help during an emergency. Other PERS have been developed that include connections with external systems, such as a central monitoring center. These types of PERS, however, do not include robust methods of communication, the capability to scale with the addition of new subsystems, advanced methods of sensing or detection, comprehensive analytical capability, or clinically useful feedback.

SUMMARY OF THE INVENTION

It is, therefore, an object of the present invention to provide for more effective monitoring of key indicators that will allow more reliable early warning to reduce loss of life, medical complications, pain, suffering, loss of independence, and medical costs. This invention aims to supplement and/or replace live caregivers and nurses by substantially improving and expanding continual oversight and quality of care, resulting in promotion of early intervention and expedited response during emergencies, and to assess and evaluate methods of care and their impact on patient improvement, stability, or decline. The invention will improve access to knowledge and care for both care providers and end-users of the invention. Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

The present invention has been developed in response to the contemporary state of health monitoring. Problems and needs requiring health monitoring have not yet been fully solved by currently available PERS. The present invention is intended to provide a comprehensive method of electronic caregiving support, health oversight and emergency response. The benefits to families and individuals seeking these protections are amplified for those who are at high risk, chronically ill, physically impaired, mentally impaired, or rehabilitating end users.

The present invention includes a front end Electronic Caregiver system of sensing devices and user interaction, and a back end Electronic Caregiver system providing an automated process to navigate responses to situations on the front end system. The Electronic Caregiver may interface with portable devices such as a tablet, a wearable device, or a mobile phone, all of which may be equipped with accelerometers, gyroscopic or movement sensors, or microprocessors. Software applications on the portable devices will maximize the capability of the Electronic Caregiver back end system and be capable of displaying updated information received from such back-end system as well as initiating other algorithms, programs and processes.

For example, in a home safety and health monitoring system, a network of devices transmit information relating to an individual's physics, gait, activity, inactivity, metal behavior, and health activities to the Electronic Caregiver system. These devices may include biomechanical detection sensors, wearable accelerometers, gyroscopic. sensors, tilt sensors, visual analytical monitoring devices, wireless ubiquitous monitoring devices, under foot pressure sensors, all of which will provide the back end of the Electronic Caregiver system data that can be assigned a biomechanical meaning.

The front end of the Electronic Caregiver system will then communicate notifications and other feed back to the end user or external parties such as central monitoring stations, health providers, and/or family members.

Figure 1:
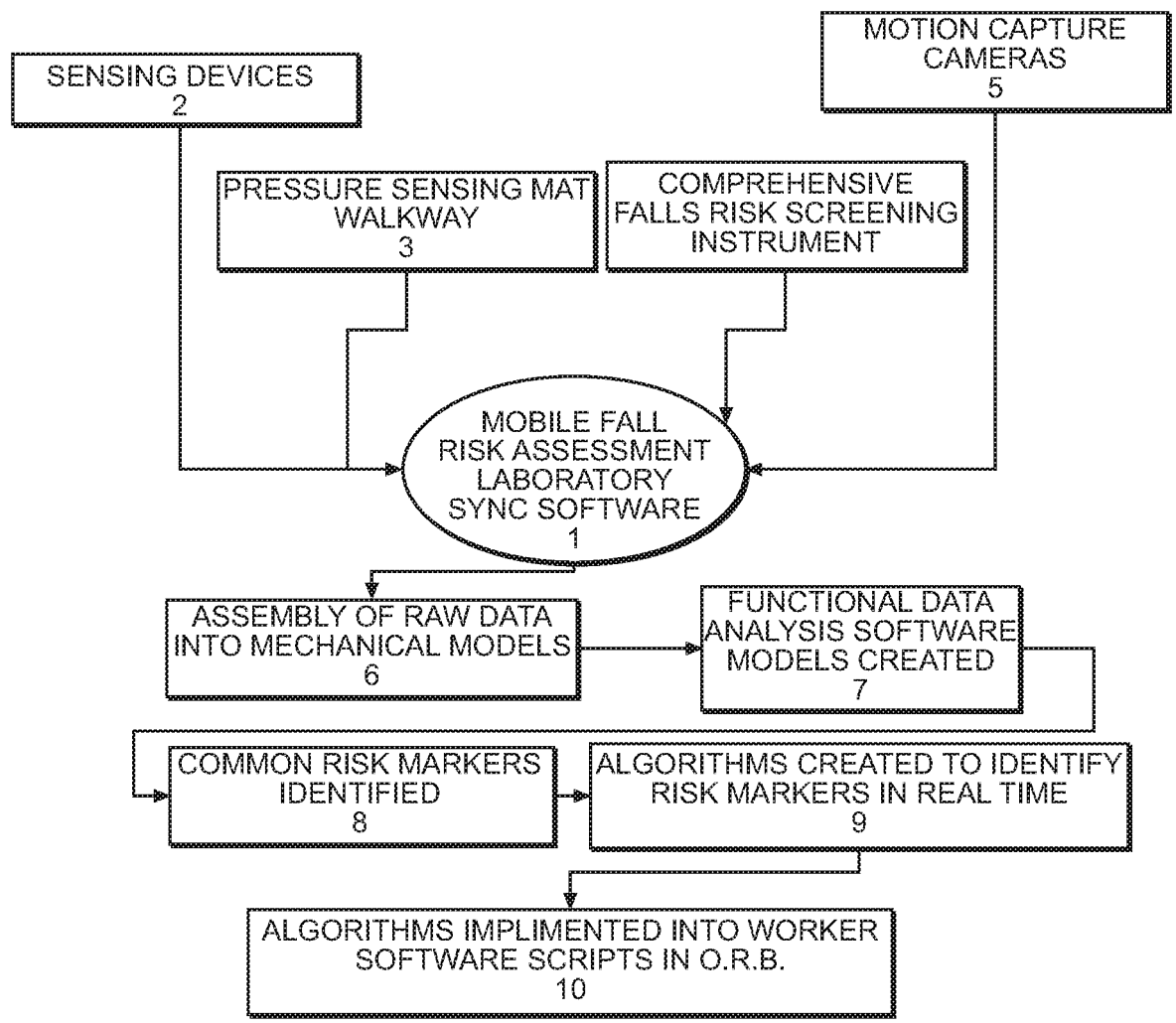
FIG. 1 is a flow chart showing the process necessary to create risk scores for new devices utilizing a golden standard of established methodology.
Figure 2:
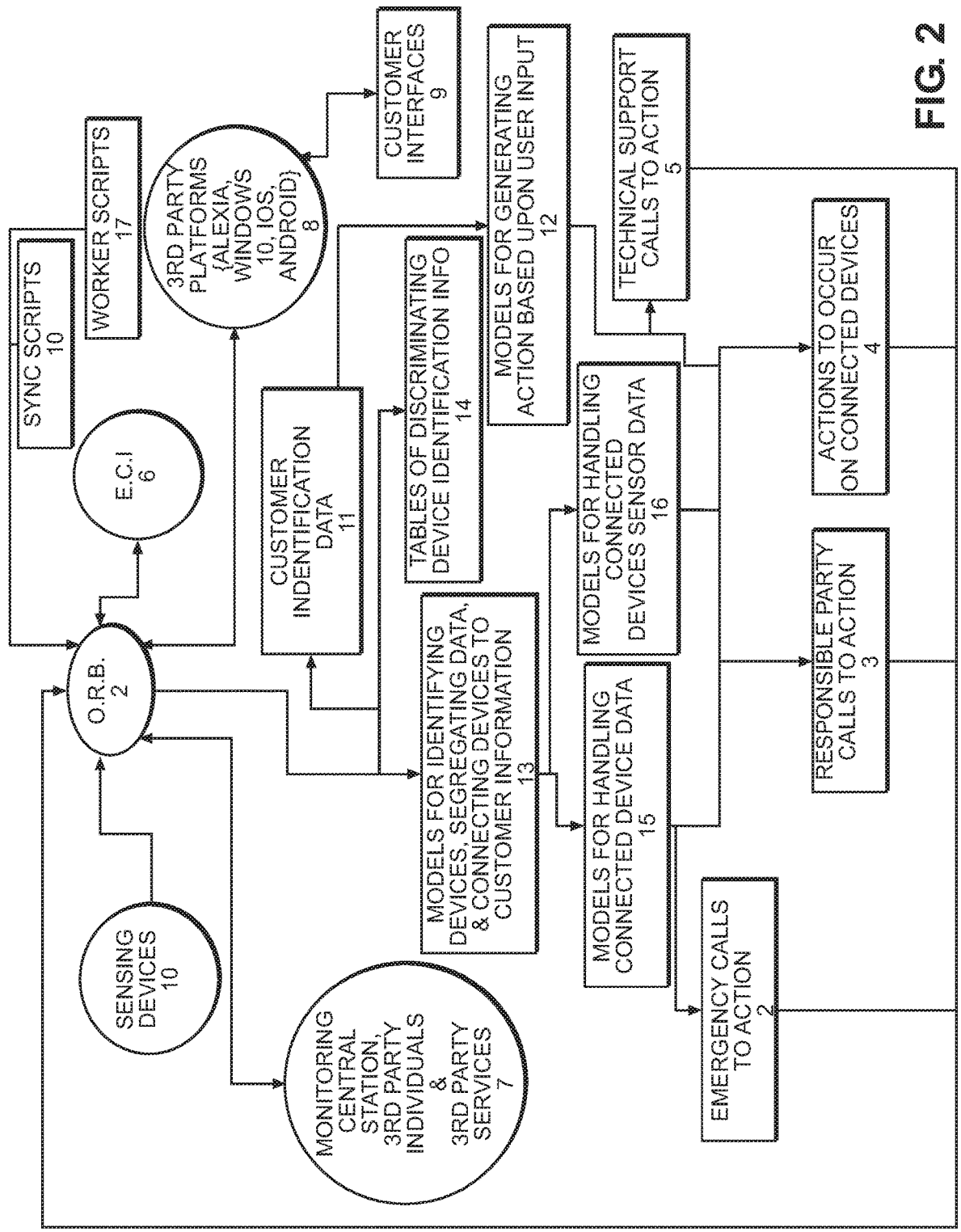
FIG. 2 is a flow chart showing the process for properly handling information from a variety of sensing devices across a variety of platforms via the Electronic Caregiver Optimum Recognition Blueprint.
Figure 3A:
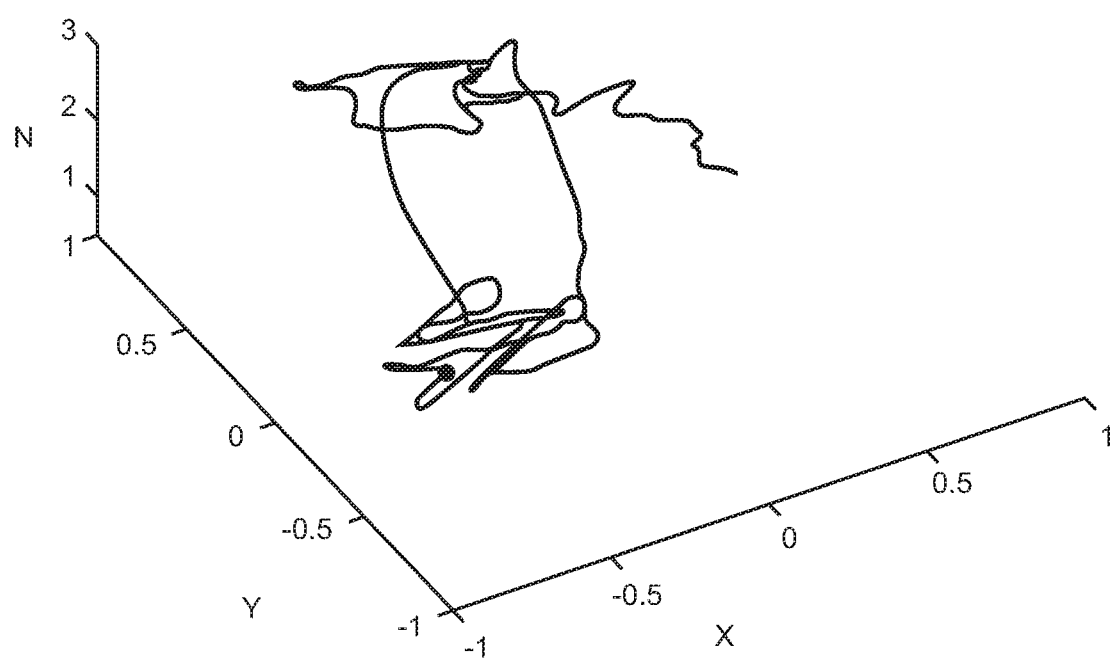
FIGS. 3A-3D illustrate the tracking of head movement during a fall as captured from a depth camera.
Figure 3B:
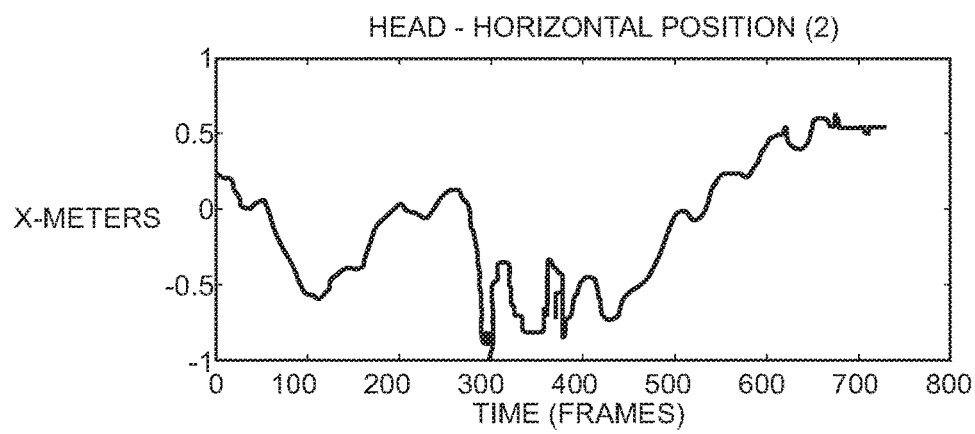
Figure 3C:
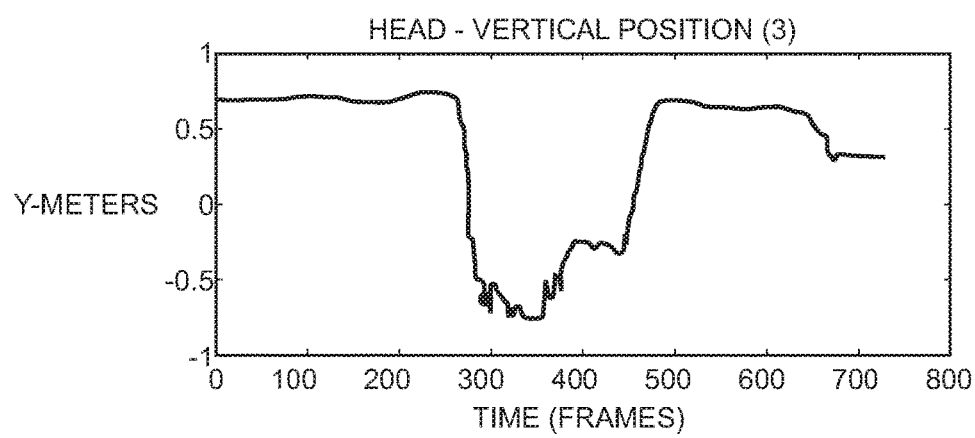
Figure 3D:
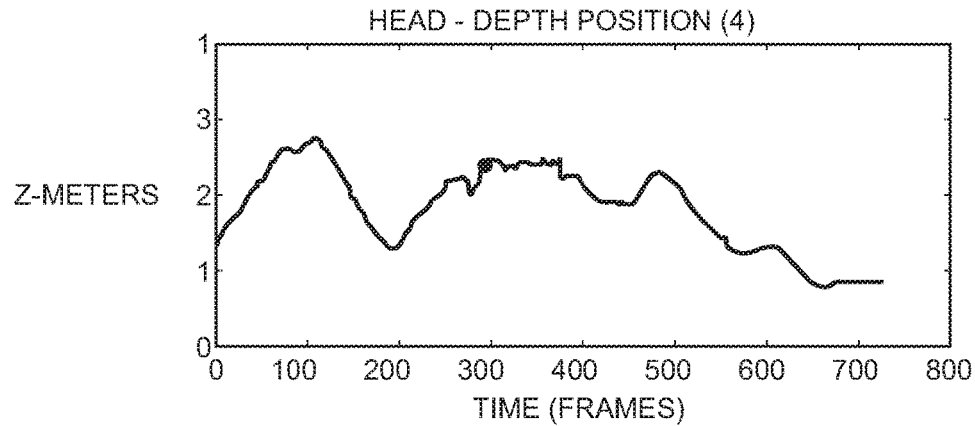
Figure 4A:
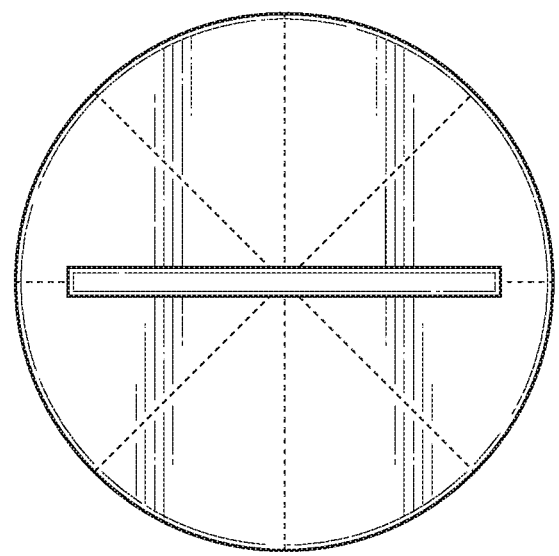
FIGS. 4A-4C are drawings of a pill box that dispenses appropriate amounts of medications at prescribed times, featuring a camera that sends data to the Electronic Caregiver Optimum Recognition Blueprint for visual analytics. This version includes a tablet for visual display of the Electronic Caregiver Image.
Figure 4B:
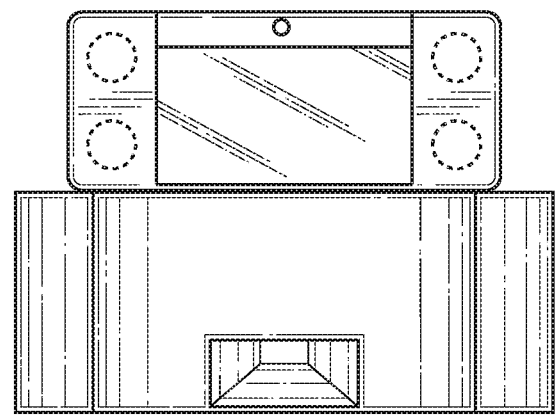
Figure 4C:
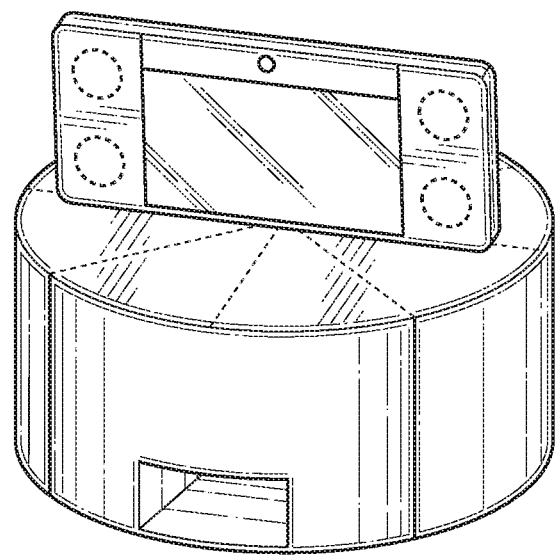
Figure 5:
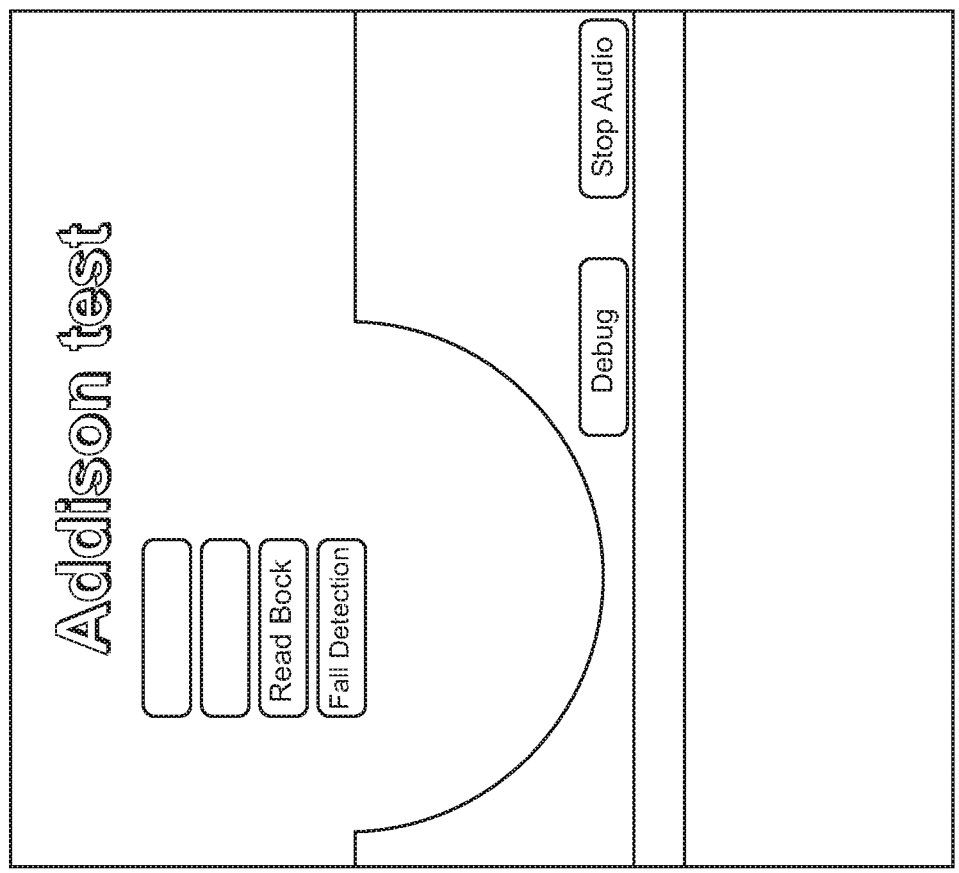
FIG. 5 is a test demonstration of functioning actions connected via Lambda functions to a personal assistant service, activated via voice prompt. These buttons are unseen by the end user of the system but utilized to connect the Electronic Caregiver Image to the Electronic Caregiver Optimum Recognition Blueprint and personal assistant services.
Figure 6:
FIG. 6 is an illustration of one embodiment of the present invention, where an Electronic Caregiver Image named Addison appears on a tablet below a depth camera inside a home, ready to monitor the well-being of the end-user and communicate with them.
Figure 7:
FIG. 7 is an illustration of one embodiment of the present invention, where an Electronic Caregiver Image named Addison speaks to an end-user regarding the status of user's medication compliance schedule.

The back end of the Electronic Caregiver is the Optimum Recognition Blueprint ("ORB") depicted as item 1 in FIG. 2. The ORB is a mapped structure of models, objects, scripts, connections, and programs which manage users, devices, and data. The ORB may include connections which add mapping of additional objects and data obtained from responders or assessment parties such as monitoring services, customer services, health services, and insurance, as depicted in FIG. 2, item 7. Data received by the ORB from the Electronic Caregiver front end, including software applications running on portable devices (FIG. 2, item 8) is mapped to the appropriate data location and is responded to, compared, interpreted, analyzed, shared, or stored based upon the model of behaviors. (FIG. 2, item 17).

The data extracted from visual detection and other motion based devices are interpreted by the ORB. The ORB determines the appropriate method for processing the data received from the device and determines the customer identification data specific to that device (FIG. 2, item 11). For example, the ORB can determine whether the data is received from a sensor such as an accelerometer (FIG. 2, item 10), a newly connected depth camera or simply device data such as low battery life on a mobile phone. In the event the ORB detects low battery life, it can issue a warning to the user and communicate with other responsible parties to alert them that the connection with the Electronic Caregiver will be lost unless the device is charged. (FIG. 2, item 15).

The ORB can initiate an emergency call to action (FIG. 2, item 2) which includes communicating to a monitoring central station (FIG. 2, item 7) the necessary information to dispatch emergency services. The ORB can initiate technical support calls as well. (FIG. 2, item 5). These types of action include equipment trouble signals. (FIG. 2, item 3). The ORB can initiate a message to immediate users on location with the front end of the system (FIG. 2, item 4) and to external parties (FIG. 2, item 7) to provide diagnosis and warning of patterns of pain, distress, injury, incapacitation, inactivity, impaired activity, mortality, medical emergency, increased or decreased risk of fall, improving health related behavioral patterns, and other wellness/treatment plans.

In one embodiment, the present invention may include visual recognition hardware such as video cameras, depth cameras, infrared cameras, thermal cameras, proximity detectors, motion capture devices (FIG. 2, item 10).

The visual recognition firmware is systematically integrated upon ORB objects containing the unique models of the present invention (FIG. 2, item 15) that utilize the Electronic Caregiver's algorithms to detect and identify physical characteristics that may indicate various musculoskeletal, cardiac, and neurological events or patterns of gait or movement. Methodology is also capable of utilizing data from visual recognition devices to detect environmental hazards including stoves, ovens, and appliances reaching unsafe temperatures or left on unattended, laundry room and kitchen fires, and unsafe ambient temperatures. Certain data identified and processed can be communicated to end users, health service providers, live caregivers, and industrial or scientific parties.

Depth cameras provide the ORB with two data sets, one that is based upon movement markers assigned to the head, spine, and joint locations, and a second data set that is based upon volume. This data is then processed through the Electronic Caregiver to assign meaning.

In addition to observing gait changes over time and creating alerts when markers are observed the ORB can create alerts when an accidental fall occurs. Data observed through a depth camera with accidental falls are two dimensional observations of rapid acceleration in movement markers followed by rapid deceleration, which can be coupled with rapid change in direction. (FIGS. 3A-3D). Depth camera data provides a third method of accidental fall verification by looking for volume in the area of the observed fall over time.

In another embodiment of the present invention, the ORB is connected to portable or wearable devices such as a Bluetooth™ emitting beacon, mobile phones, wearable video recorders, wearable fitness and activity devices, and other health related devices, and may use wired or wireless pathways of communication between it and the devices. (FIG. 2, item 8).

Using an installed Electronic Caregiver software application and associated ORB objects containing data processing models utilizing algorithms, a variety of alerts, signaling parameters, one way and two way communications can be programmed and initiated, including summoning response when patterns of activity become irregular or suspicious.

In another embodiment of the present invention, ORB objects contain models to process and present an Electronic Caregiver Image ("ECI"). (FIG. 2, item 6). The ECI utilizes ORB objects containing processing capabilities of a personal assistant including the capability to leverage and integrate with third party personal assistant systems. The ECI appears as an animated figure emulating a live action caregiver, and is presented on tablets with cameras that provide visual recognition described above while running firmware connected to Electronic Caregiver back end systems. The ECI also appears on media or video screens, or devices containing presentation capability, such as mobile phones, wearable devices, and existing television or computer monitors. The ECI may appear in strictly auditory format in applications where this is found to better meet user or platform needs.

The ECI may provide dietary or medication reminders, appointment reminders, and may act as a sincere, caring or humorous companion. The ECI can present companionship, and identify and display medications or health test equipment, and can engage in an exchange between device and end user that results in an experience that appears life like and intelligent. The ECI relies upon the Electronic Caregiver ORB system and algorithms, and may learn end user behaviors, likes and dislikes, resulting in modified preprogrammed behaviors and a more pleasing interactive experience.

The ECI interface and algorithms may receive input from 2-way audio and/or visual devices. When visual or audio devices detect a need for intervention, the ECI can respond to verbal and physical cues from the end user and may respond accordingly, including initiating a video, audio or other method of dialog between the end user and an external party. ECI features, security and permissions are established using a simple applications based user interface.

In another embodiment of the present invention Electronic Caregiver ORB systems are connected to visual or audio recognition devices, or heat and fluid sensors, and can detect and signal the Electronic Caregiver front end and the ORB in response to running water, fire, temperature, status of appliances, and may also detect movement and the opening of windows and doors. Detection of the above mentioned conditions may result in communications initiated to the end user or third parties.

In another embodiment of the present invention, the ORB is connected through the Electronic Caregiver front end to devices such as visual or audio recognition devices, or pressure or sensors that can detect the opening or closing of containers. Using the Electronic Caregiver algorithms, the sensing devices can monitor a medication organizer or dispenser and record usage, dosage, or may warn if the end user is attempting to access the wrong medication or dosage.

In another embodiment of the present invention, the Electronic Caregiver back end is connected through the Electronic Caregiver front end to devices such as mobile phones or portable/wearable activity or health monitoring devices, providing a Health Direct Link and integrated application. The Electronic Caregiver algorithms and applications provide an easy to access one touch feature to access an immediate link to an external third party during a medical emergency, and geo-positioning monitoring may be activated to locate the end user. This feature provides an option by mode selection of the application to initiate non-emergency connections to an external third party such as a health professional or emergency responder during a medical concern such as trouble breathing, trouble swallowing, head pain, abdominal pain or an escalation in these conditions.

The ECI will include a standard of care assessment module. Through an automated, integrated array of stationary and at least one of a wearable technology sensor or detector, such as ground reaction sensing, medical peripherals which may include thermometer, blood pressure device, glucometer, pulse 02 sensor, weight scale, spirometer, glucometer, digital camera, laser, depth and thermal cameras, and at least one facial or body recognition interpretive device, verbal, audible and physical feedback systems, and a display monitor or projection. The system will monitor and assess symptoms and indicators of improvement, stability or decline to physical or mental health status. The system uses a combination of artificial caregiver projected or displayed imagery, and natural language engines, coupled with artificial intelligence software, machine learning and at least one of an in-home or on-body device to monitor and enable real time patient assessments, interventions and reports. The system is used to supplement or replace a live physical caregiver to prompt, analyze and respond to both standard and proprietary symptomatic diagnostic formulas.

The system identifies and interprets health symptoms and status indicators such as hydration, bathroom usage and type, wake and sleep patterns, activity and inactivity characteristics and type, biomechanical and movement diagnostics, mood and mental state assessments, dietary and nutrition activity, vital readings and statistics, interrogatory responses and both standard and non-standard indicators necessary to monitor health performance, stability or decline. Real time monitoring is uploaded into real time cloud diagnostic and assessment software to interpret required responses and interventions to recommend or implement methods of care, suggested improvements to standards of care, to identify non-working methods and standards of care, to compare and evaluate various standards of care, and to notify and report to specific or interdisciplinary parties that can engage to improve patient health and wellness outcomes. System may also be programmed to advise and inform technology, pharmacology, device, software or physical care providers or parties of relevant data for the purposes of disclosing poor performance products, services or patient responses, as well as improvements, trends and recommendations to compel advanced innovation for patient care and service.

In one embodiment of the present invention, ORB initiates shipment of a pharmacogenetic saliva sample kit as soon as a Virtual Caregiver System (VCS), a tablet & depth camera combination system featuring the ECI, is placed on order. The patient will be prompted by the ECI and shown instructions by the ECI on how to complete the swab and saliva sample and mail the kit to the lab. The lab conducts the genetic screening and will electronically forward a report to the ORB to store the genetic profile information and results. The ECI alerts the patient via home care alerts and tablets, and conducts the pharmacology consultation with the patient, making recommendations on updating their medications if necessary based on test results, and metabolic drug scoring. Replacement medications are then entered or scanned into the ORB using the localized ECI, and recognized by the software as a replacement drug, whereby the reminders and monitoring system is updated. A report is available to print for primary care physician, pharmacist or related health specialist.

In another embodiment of the present invention, the ORB is connected through the Electronic Caregiver front end to devices such as mobile phones, computers or tablets, onto which is displayed a Comprehensive Falls Risk Screening Instrument ("CFRSI"), which includes proprietary algorithms to process user information inputs to produce a diagnostic output. THE CFRSI uses a process to collect history information, range of motion data, and other key indicators to identify and publish a fall risk profile and assessed score and grading profile. This data is then referenced against other pertinent data collected from the end user's mobile phone, wearable device, or information collected from visual recognition devices or pressure sensing devices.

In another embodiment, the ORB collects and stores data in cumulative storage locations. Machine learning algorithms are then incorporated to assess data received from all participating end users. All is compared and processed to output information to improve health awareness.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for automated fall detection and reporting via a virtual system, the virtual system comprising at least one processor configured to execute the method comprising:
   receiving, at a processor in the virtual system, from a depth camera configured to be pointed at a human, a first data set of virtual movement markers comprising a cluster of data points in a shape of a body of the human,
   the first data set of virtual movement markers comprising a first movement marker estimated to a head location of the human, a second movement marker estimated to a spine location of the human, and a third movement marker estimated to a joint location of the human;
   receiving, at the processor in the virtual system, from the depth camera a second data set indicating volume in an area of a location of the human:
   detecting, at the processor in the virtual system, from an accelerometer, a rapid acceleration of at least two of the movement markers comprising the first data set of virtual movement markers, followed by a rapid deceleration of at least two of the movement markers comprising the first data set of virtual movement markers, wherein at least one of the rapid acceleration and the rapid deceleration includes a rapid change in direction of the location of at least one of the movement markers comprising the first data set of virtual movement markers;

detecting, at the processor in the virtual system, an irregular pattern of activity for the human from changes in the first data set of virtual movement markers and the second data set; and sending, at the processor in the virtual system, an alert to a reporting device indicating that the human has fallen based on the detected irregular pattern of activity.

2. The method of claim 1, further comprising processing the first data set and the second data set from the depth camera against an optimum recognition blueprint.

3. The method of claim 1, wherein the alert to the reporting device comprises a communication from the virtual system to a monitoring central station with necessary information to dispatch local emergency services to the location of the human.

4. The method of claim 1, wherein the alert to the reporting device comprises a communication from the virtual system to a user computing device warning that the human has fallen.

* * * * *

UNITED STATES PATENT AND TRADEMARK OFFICE
CERTIFICATE OF CORRECTION

PATENT NO. : 10,813,572 B2  
APPLICATION NO. : 15/530185  
DATED : October 27, 2020  
INVENTOR(S) : Anthony Dohrmann et al.

Page 1 of 1

It is certified that error appears in the above-identified patent and that said Letters Patent is hereby corrected as shown below:

On the Title Page

Item (72) Inventors, that portion reading:  
-Robert Salcido-  
Should read:  
--Roberto Abel Salcido--

Signed and Sealed this  
Eleventh Day of January, 2022

Drew Hirshfeld  
*Performing the Functions and Duties of the*  
*Under Secretary of Commerce for Intellectual Property and*  
*Director of the United States Patent and Trademark Office*